United States Patent
Chen

(10) Patent No.: US 10,115,238 B2
(45) Date of Patent: *Oct. 30, 2018

(54) METHOD AND APPARATUS FOR RECOGNIZING BEHAVIOR AND PROVIDING INFORMATION

(71) Applicant: Alexander C. Chen, La Canada-Flintridge, CA (US)

(72) Inventor: Alexander C. Chen, La Canada-Flintridge, CA (US)

( * ) Notice: Subject to any disclaimer, the term of this patent is extended or adjusted under 35 U.S.C. 154(b) by 124 days.

This patent is subject to a terminal disclaimer.

(21) Appl. No.: 15/331,834

(22) Filed: Oct. 22, 2016

(65) Prior Publication Data

US 2017/0069139 A1 Mar. 9, 2017

Related U.S. Application Data

(63) Continuation of application No. 14/182,297, filed on Feb. 18, 2014, now Pat. No. 9,500,865.

(Continued)

(51) Int. Cl.

| | |
|---|---|
| *G06T 9/00* | (2006.01) |
| *H04N 5/272* | (2006.01) |
| *H04M 1/725* | (2006.01) |
| *A61B 5/00* | (2006.01) |
| *A61B 5/11* | (2006.01) |
| *G06Q 50/00* | (2012.01) |
| *G06Q 30/02* | (2012.01) |
| *G02B 27/01* | (2006.01) |
| *G06T 19/00* | (2011.01) |
| *A61B 5/08* | (2006.01) |

(Continued)

(52) U.S. Cl.
CPC .......... *G06T 19/006* (2013.01); *A61B 5/0022* (2013.01); *A61B 5/11* (2013.01); *A61B 5/6803* (2013.01); *G02B 27/017* (2013.01); *G06Q 30/0267* (2013.01); *G06Q 50/01* (2013.01); *H04M 1/7253* (2013.01); *H04N 5/272* (2013.01); *A61B 5/082* (2013.01); *A61B 5/0823* (2013.01); *A61B 5/1116* (2013.01); *A61B 5/165* (2013.01); *A61B 5/18* (2013.01); *A61B 5/745* (2013.01); *A61B 2560/0242* (2013.01); *G02B 2027/0138* (2013.01); *G02B 2027/0178* (2013.01); *H04M 2250/52* (2013.01)

(58) Field of Classification Search
CPC ............ H04N 5/272; H04N 2005/2726; G06T 19/006; G02B 27/017; G06Q 50/01
See application file for complete search history.

(56) References Cited

U.S. PATENT DOCUMENTS

| | | | |
|---|---|---|---|
| 7,801,332 B2 * | 9/2010 | Albertson | .......... G06K 9/00979 382/107 |
| 8,577,087 B2 * | 11/2013 | Albertson | .......... G06K 9/00335 382/103 |

(Continued)

FOREIGN PATENT DOCUMENTS

JP 2012000449 A * 1/2012

*Primary Examiner* — John Villecco

(57) ABSTRACT

A method and apparatus may capture an image of a second person with a camera on a frame worn by a user, transmit the image to a second device, receive a recommendation for the user to interact with the second person in response to a behavior of the second person, and display the recommendation to the user on how to interact with the second person in response to the second person's behavior.

20 Claims, 10 Drawing Sheets

Related U.S. Application Data

(60) Provisional application No. 61/771,943, filed on Mar. 4, 2013.

(51) Int. Cl.
*A61B 5/16* (2006.01)
*A61B 5/18* (2006.01)

(56) References Cited

U.S. PATENT DOCUMENTS

| | | | | | |
|---|---|---|---|---|---|
| 8,615,479 | B2* | 12/2013 | Jung | | A61B 5/04842 706/46 |
| 8,743,145 | B1* | 6/2014 | Price | | G06T 19/006 345/629 |
| 8,894,484 | B2* | 11/2014 | Latta | | A63F 13/211 463/29 |
| 9,019,174 | B2* | 4/2015 | Jerauld | | A61B 5/486 345/8 |
| 9,183,356 | B2* | 11/2015 | Seo | | A61B 5/021 |
| 9,508,008 | B2* | 11/2016 | Jerauld | | A61B 5/486 |
| 9,778,734 | B2* | 10/2017 | Kim | | G06F 3/00 |
| 9,824,698 | B2* | 11/2017 | Jerauld | | G10L 25/63 |
| 2007/0229663 | A1* | 10/2007 | Aoto | | G06K 9/00335 348/155 |
| 2009/0006286 | A1* | 1/2009 | Angell | | G06K 9/00771 706/12 |
| 2012/0019557 | A1* | 1/2012 | Aronsson | | G06T 11/00 345/633 |
| 2013/0009993 | A1* | 1/2013 | Horseman | | G16H 40/63 345/633 |
| 2013/0044130 | A1* | 2/2013 | Geisner | | G09G 5/00 345/633 |
| 2013/0095460 | A1* | 4/2013 | Bishop | | G09B 21/009 434/308 |
| 2013/0137076 | A1* | 5/2013 | Perez | | G09B 5/06 434/308 |
| 2013/0202210 | A1* | 8/2013 | Ryoo | | G06K 9/00771 382/195 |
| 2014/0063055 | A1* | 3/2014 | Osterhout | | G06F 3/005 345/633 |
| 2014/0118225 | A1* | 5/2014 | Jerauld | | A61B 5/486 345/8 |
| 2014/0139551 | A1* | 5/2014 | McCulloch | | G09G 5/377 345/633 |
| 2014/0149177 | A1* | 5/2014 | Frank | | G06Q 10/06 705/7.29 |
| 2014/0160157 | A1* | 6/2014 | Poulos | | G06F 3/011 345/633 |
| 2014/0222462 | A1* | 8/2014 | Shakil | | G06Q 50/22 705/3 |
| 2014/0222526 | A1* | 8/2014 | Shakil | | G06Q 50/22 705/7.38 |
| 2014/0266647 | A1* | 9/2014 | Visitacion | | G08B 6/00 340/407.1 |
| 2014/0306994 | A1* | 10/2014 | Brown | | G06T 19/006 345/633 |
| 2014/0323817 | A1* | 10/2014 | el Kaliouby | | A61B 5/165 600/300 |
| 2015/0040036 | A1* | 2/2015 | Crocker | | G06F 3/04815 715/757 |
| 2015/0128096 | A1* | 5/2015 | Rizvi | | G02B 27/017 715/863 |
| 2015/0242707 | A1* | 8/2015 | Wilf | | G06K 9/00302 382/159 |
| 2015/0338912 | A1* | 11/2015 | Kim | | H04N 5/91 345/520 |
| 2016/0048990 | A1* | 2/2016 | Seo | | G06T 11/60 345/632 |
| 2016/0263477 | A1* | 9/2016 | Ladd | | A63F 13/26 |
| 2017/0103564 | A1* | 4/2017 | Hayashida | | G06F 3/048 |
| 2017/0117005 | A1* | 4/2017 | Jerauld | | G10L 25/63 |
| 2018/0108347 | A1* | 4/2018 | Ogata | | G10L 15/1815 |

* cited by examiner

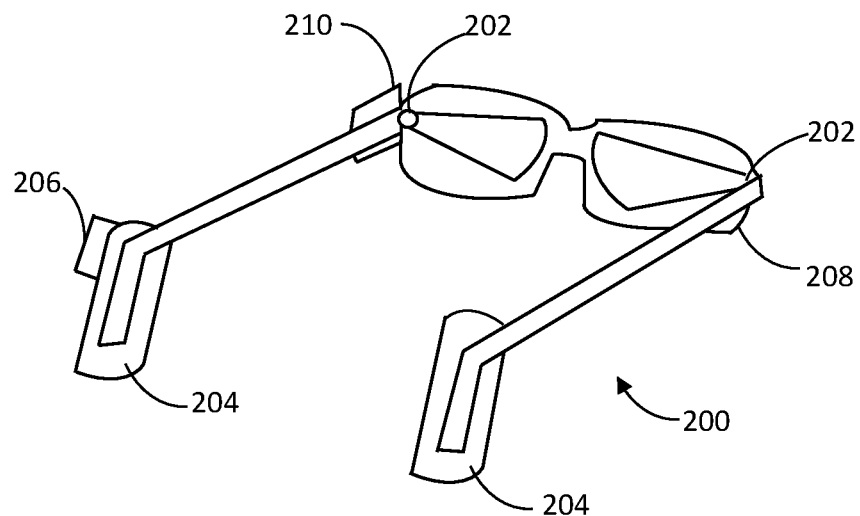
FIG. 2A BACK VIEW
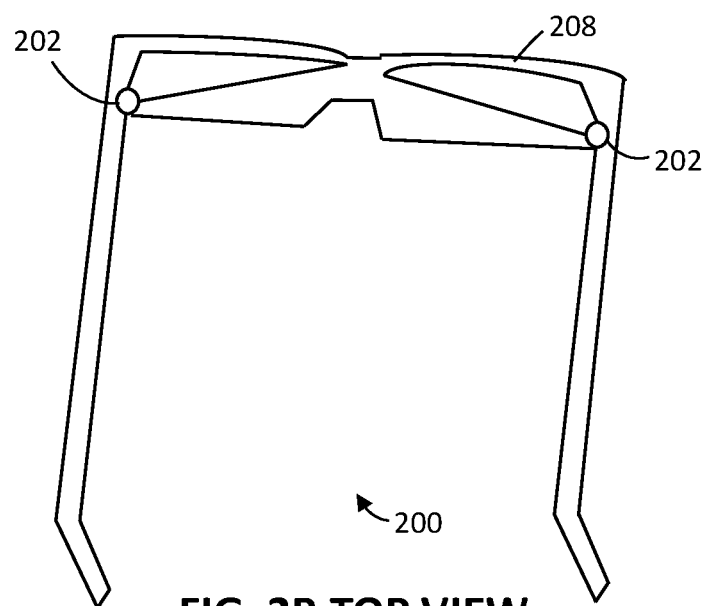
FIG. 2B TOP VIEW

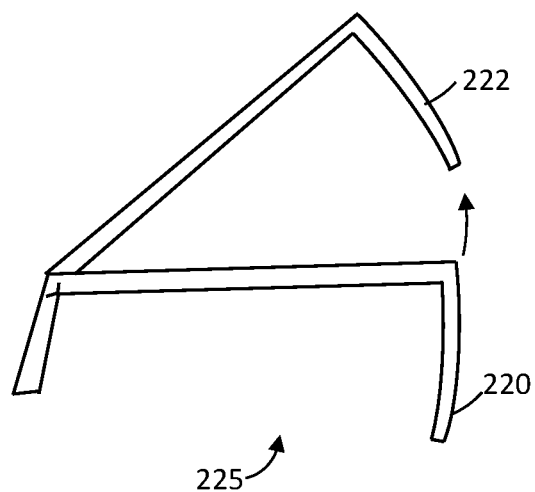
FIG. 2C SIDE VIEW

METHOD AND APPARATUS FOR RECOGNIZING BEHAVIOR AND PROVIDING INFORMATION

CLAIM OF PRIORITY

This is a continuation patent application of U.S. patent application Ser. No. 14/182,297, entitled "Method and Apparatus for Recognizing Behavior and Providing Information," filed on Feb. 18, 2014, which claims priority to U.S. Provisional Application No. 61/771,943, entitled "Method and Apparatus for Sensing and Displaying Information," filed on Mar. 4, 2013, which are both hereby incorporated herein by reference in their entireties.

FIELD

This application relates to devices that sense and display information.

BACKGROUND

Cell phones, tablet computers, and laptop computers receive and display information.

BRIEF DESCRIPTION OF THE FIGURES

FIGS. 2A and 2B show back and top views of a pair of glasses.

FIG. 2C shows a side view of a pair of glasses.

DESCRIPTION

Figure 8A:
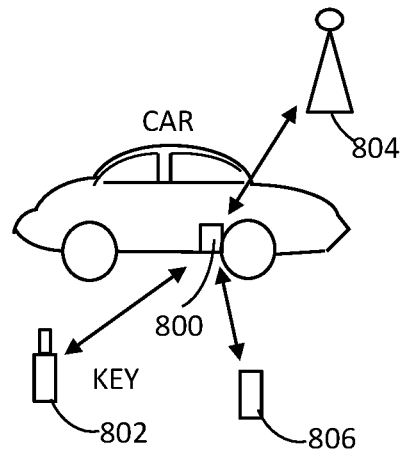
FIG. 8A shows a device that can sense when a user's item is moved.
Figure 8B:
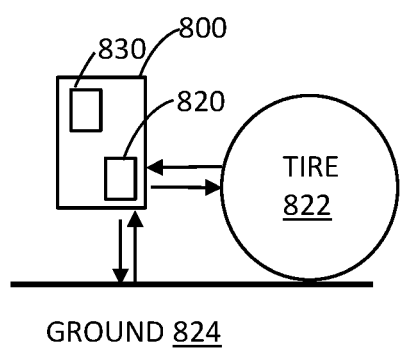
FIG. 8B shows a device with a transceiver that detects a user key.
Figure 9:
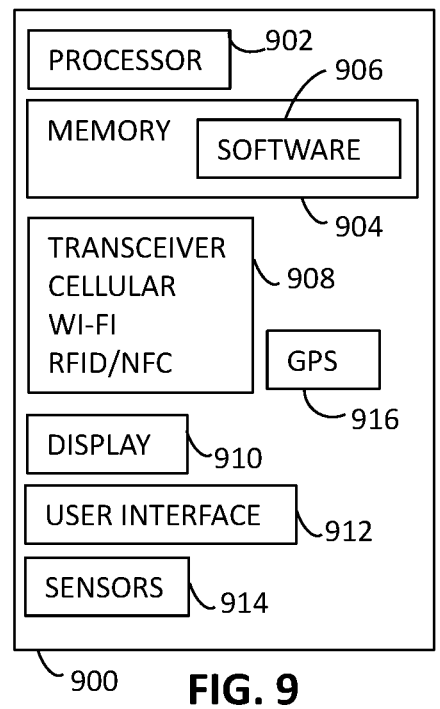
FIG. 9 shows a device that represent the devices in FIGS. 1A-8B and 10.

1. Mobile Device that Projects An Image or Video
2. Glasses that Generate Viewable Information on Lenses
3. Sensors for Sports
4. Sensors in car to detect drunk driving
5. Location-specific Communication Device
6. Multi-media Interactive Dating Experience
7. Mobile Phone Jamming Device
8. Motion Detection and Alert System FIG. 9 shows a device 900, which may represent any of the devices in FIGS. 1A-8B described below. The devices in FIGS. 1A-8B may comprise one or more of the elements shown in FIG. 9 and/or additional elements, depending on the desired cost, size, and functions of each device. The device 900 may represent a mobile phone, a tablet computer, a laptop, a display, a wristwatch, a game console, a car key, a key chain, or a remote control to control another device, such as a TV, stereo, display, or car.

The device 900 may comprise a processor 902, a memory 904, a wireless transceiver 908 (e.g., 2G or 3G cellular, Long Term Evolution (LTE), WiMAX, WiFi, Bluetooth, RFID, Near Field Communication (NFC), etc.), a display 910, a user interface 912, one or more sensors 914, and a global positioning system (GPS) chip or other position tracking system 916. The user interface 912 may include one or more physical keys or buttons, and/or a menu of options shown on the display 910, such as a touchscreen.

The sensors 914 may sense one or more conditions of the environment (such as amount of visible or invisible light, temperature, humidity, odors, sounds, touch, amount of particles in the air, such as plant pollen) and/or objects (or characteristics of the objects) around the device 900, such as motion, color, shape, size, surface type, distance from the device 900.

The memory 904 may store one or more software modules 906 that can be executed by the processor 902 to perform some or all of the functions described below.

The device 900 may communicate directly with a server or computer or indirectly via a wireless network to download software apps and transmit and receive information.

Data transmitted from one device to another device or network, as described below, may be encoded (such as CDMA) or encrypted for security.

An image as described below may refer to a single image or a series of images such as a video.

1. Mobile Device that Projects an Image or Video

A. Projecting on a Surface

Figure 1A:
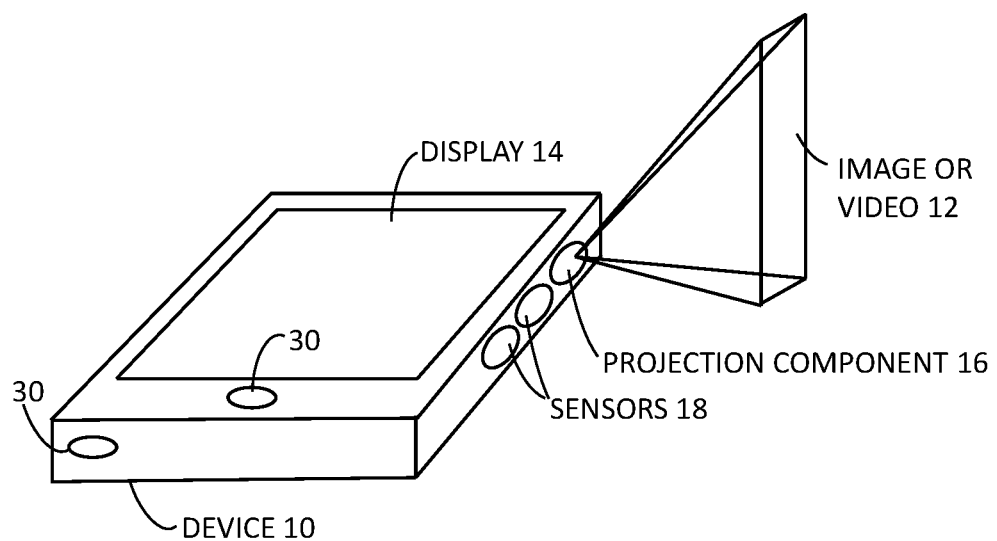
FIG. 1A shows a device with a projection component to project an image.

FIG. 1A shows a device 10 (such as a mobile phone or tablet) with a projection component 16 to project an image or video 12 on a wall or other surface.

Projection Component

The projection component 16 may comprise one or more lasers (such as red, green, blue or RGB or other color configurations), microelectromechanical systems (MEMS), lenses, filters (such as movable color filters), polarizers, reflectors (such as mirrors), diffraction elements, refraction elements, beam splitters, light-emitting diodes (LEDs), and/or other optical elements, etc. The projection component 16 may be sufficiently low power such that it is not harmful to people.

Wall or Surface

The wall or surface may be flat, textured or uneven, or non-flat, such as curved ball. The wall or surface may be segmented or partially flat, and partially non-flat. The surface may be any color, such as white, off-white, and gray, black.

One advantage of the device 10 is that the projected image or video 12 can be larger than the mobile device's display 14, so more users can view the projected image (such as a calendar, a spreadsheet, or Powerpoint presentation) or video (such as a game, a music video, a movie, a scene from a movie, or a movie trailer) 12.

User Interface

The device 10 may have a user interface (such as buttons or keys 30, a keypad, and/or a menu or icons on a touch-screen or display 14) that allows a user to control the projected image or video 12, such as start, stop, pause, fast forward, rewind, and/or adjust one or more parameters of the projection component 16, such as light intensity/brightness, color, contrast, focus, sharpness.

The entire display 14 or a portion of the display 14 may show the same image or video as the image or video 12 being projected. In another example, the display 14 may show a different image or video (such as a first scene or character from a movie or game) than the projected image or video 12 (such as a second scene or character from the movie or game). In another example, the display 14 may show statistics of one or more sports players or video game characters, while the projected image or video 14 may show the one or more sports players or video game characters.

Sensors

The device 10 may have one or more sensors 18 that sense one or more conditions of the environment (such as amount of visible or invisible light, temperature, humidity, odors, sounds, touch) or objects (or characteristics of objects) around the device 10, such as motion, the presence of a person's hand or face, one or more characteristics of the wall (such as a color, shape, size, surface type of the wall), a distance to the wall from the device 10, etc. After the sensor 18 senses one or more of these conditions, the device 10 may adjust one or more parameters of the projection component 16, such as light intensity, color, contrast, focus, sharpness, which may change the image or video 12.

For example, the sensor 18 may sense a person's hand or face near the device 10, and the device 10 may decrease the light intensity of the projector component 16 or stop the projection.

As another example, the sensor 18 may sense that the wall or surface has a picture (such as a hand-drawn picture, a computer-generated image (CGI), or a photograph). The device 10 may cause the projected image or video 12 to interact with the picture. For example, the sensor 18 may sense that the wall or surface has a picture of a house, and the device 10 may project characters that play in or around the house.

As another example, the sensor 18 may sense daylight or a well-lit room, and the device 10 may increase intensity of the projection component 16 by a fixed amount or a variable amount. The sensor 18 may sense night time or a dimly-lit room, and the device 10 may decrease intensity of the projection component 16 by a fixed amount or a variable amount.

As another example, the sensor 18 may sense the size of an available flat surface area, and the device 10 may adjust the size of the projected image or video 12.

As another example, the sensor 18 sense the color of the wall, and the device 10 may adjust one or more colors of the projected image or video 12.

As another example, the sensor 18 senses an object, such as a person's finger, a small sword, or ball, and the device 10 may cause the projection component 16 to project an animated object or character that reacts with the real object. For example, if a person uses a finger to poke an animated, projected character, the character can react by saying something or jumping.

Connection to Server or Internet

The device 10 may connect (wired or wirelessly) to a server and/or the Internet to retrieve (push or pull) images or videos (downloaded or streamed) to project on a surface. The device 10 may use a GPS chip 916 (FIG. 9) or other location-tracking system to select or modify content to retrieve and project, such as a map or local restaurant menus or advertisements. The device 10 may use user preferences (such as a selected language, type of music, name of user's preferred bank, restaurant, grocery store) to select or modify content to retrieve or project.

Power

The device 10 may receive power from one or more sources, such as a power outlet, solar power or other light sources, another device, and/or a power docking station or pad. When the device 10 runs low on power, the device 10 may cause the projected image or video 12 to change or display a low power message or symbol.

Two or More Devices

Figure 1B:
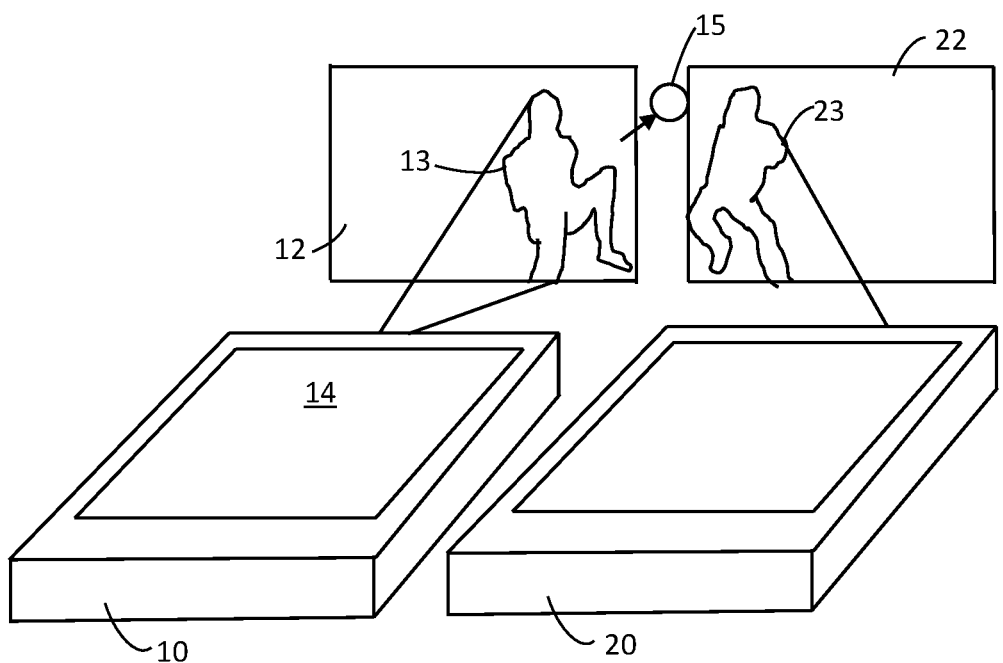
FIG. 1B shows first and second devices similar to the device of FIG. 1A.

FIG. 1B shows a first device 10 with a component (such as a NFC chip, a Bluetooth chip, and/or a WiFi chip) that senses a second device 20 near the device 10 (such as touching or bumping each other, in close proximity, or in the same room). The first and second devices 10, 20 may be similar (such as two mobile phones) or different (such as an Android phone and an iPad). When two or more devices 10, 20 are put together (either touching or in close proximity), they can project one large image (such as a widescreen movie) or two separate images. Objects or characters in the two images can interact, such as a character running from a first scene in the first projected image 12 to a second scene in the second projected image 22. As another example, a first character 13 can kick a ball 15 to a second character 23 or fight each other in a game. The two devices 10, 20 may receive commands from one or more users, such as commands to move characters projected in the two images or videos 12, 22. The two devices 10, 20 may communicate with each other (exchange commands and data; synchronize processing) to let two users play a game. Two devices 10, 20 are used here as an example, but three or more devices may be used.

An apparatus comprising:
a user interface configured to receive a request for an image;
a processor configured to process the request;
a wireless transceiver configured to send the request to a network and receive the requested image; and
a light projector configured to project the requested image on an object that is separate from the apparatus.

The apparatus of claim 2, further comprising a sensor configured to sense a condition, wherein the processor is configured to change a parameter of the light projector depending on the condition sensed by the sensor.

A method as described herein.

A method comprising:
receiving a request for an image;
sending the request to a network;
receiving the requested image; and
projecting the received image on an object.

B. Projecting a Hologram

Figure 1C:
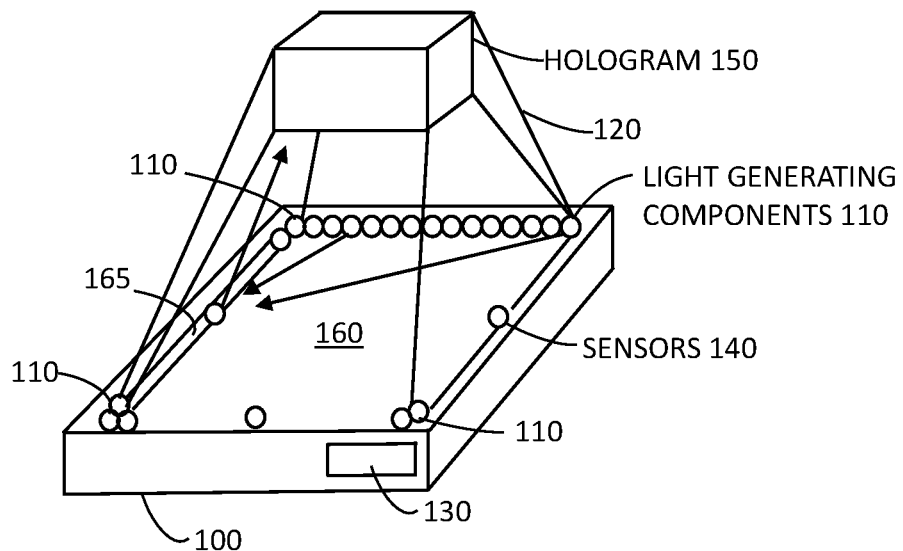
FIG. 1C shows a device with light generating components.

FIG. 1C shows a device 100 (such as a mobile phone or tablet) with light generating components 110 that generate a 3-dimensional hologram 150 (also known as a holograph or a virtual image or video) of one or more objects or characters that appears to be above the surface of the device 100. There may be several ways to do this. In one configuration, the light generating components 110 generate beams of light 120 in the air above the surface of the device 100. The light beams 120 interfere (or otherwise react) with each other to generate the hologram 150.

In another configuration, the light generating components 110 generate beams of light 120 at one or more raised sides 165 of the device 100, as shown by the two arrows pointing right to left across the display 160. The raised sides 165 may have an image or pattern (similar to a recording medium or photographic plate used for traditional holograms) that diffracts the light 120 to produce a light field and the hologram 150 above the surface of the device 100 (as shown by the arrow pointing up from the raised side 165 to the hologram 150). The raised sides 165 of the device 100 may dynamically change in appearance (such as an image or video), configuration, color, pattern, etc., so that the hologram 150 changes in appearance. The raised sides 165 may comprise a liquid crystal display (LCD) and/or one or more recording mediums for traditional holograms, such as a photographic film (silver halide photographic emulsion) with a high concentration of light-reactive grains for high resolution. A layer of this recording medium (e.g., silver halide) may be attached to a transparent substrate, such as glass or plastic. The raised edges 165 may comprise an array or small plates, which may be moved by actuators (such as MEMS) and change their angle of reflection, refraction, and/or diffraction from 0 to 180 degrees from the surface of the display 160. The angle of the raised edge 165 may affect the height of the hologram 150.

The hologram 150 may appear different from different viewing angles around the device 100. For example, if the device 100 is lying flat on a table, a person standing south of the device 100 may see the hologram of a face of a character, while a person standing east or west of the device 100 can see a side profile of the character's head.

Light Generating Components

The light generating components 110 may comprise one or more elements described above with component 16 in FIG. 1A. In addition to or instead of the elements described above with component 16 in FIG. 1A, light generating components 110 may comprise other optical elements or materials that emit, filter, and/or alter light, such as semiconductor or diode lasers.

Figure 1D:
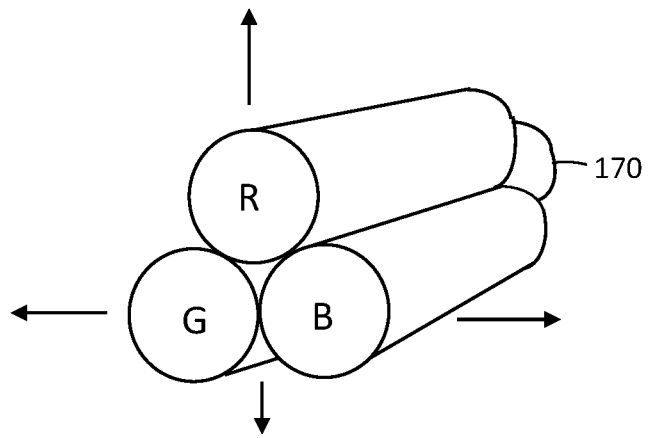
FIG. 1D shows an example of three light-generating components.

The light generating components 110 may be arranged in one or more configurations to generate a hologram 150 above the device 100. FIG. 1D shows an example of three light-generating components (red, green, blue) grouped together, which may be moved together, by an actuator 170, such as a MEMS. Other configurations may be used.

There may be any number of light generating components 110 in the corners and/or along the edges of the device 100. In one configuration, the components 110 are only in the corners. In another configuration, the components are along the sides of the device 100. In one example, the components 110 are positioned along raised edges of the device 100, where the raised edges are higher than the center surface of the device 100. In another example, the components are embedded under a top surface of the device. The components 110 may be spaced apart or close together. The components 110 may be arranged in a pattern around the edges of the device 100.

There may be more than one row of components 110 along each edge of the device 100.

The components 110 may generate light with the same or different intensity or wavelengths, such as red, blue, yellow, green, etc. In one configuration, each component 110 may be configured to change its wavelength, intensity, position, angle, or other parameter under the control of a processor 130 in the device 100.

The components 110 may move in various directions or degrees of freedom (for example, using MEMS 170) according to software executed by a processor 130. The processor 130 may control and synchronize movement of the components 110. The movement may be small (such as micrometers) and very fast (such as microseconds). Moving the components 110 in a synchronized manner may cause the hologram 150 of an object or character to move or change appearance.

Hologram

The hologram 150 may be any stationary or moving object or character, such as sports players, news updates, graphs (bar graphs, pie charts), medical simulations (such as surgeries), games, movies, advertising, etc. The hologram 150 may be black & white, gray, or in one or more other colors.

Display

The device 100 in FIG. 1C may have a display 160, such as a touch screen, as described above with the display 14 on FIG. 1A. The device 100 may display an image or video on the display 160 at the same time as the components 110 generate a hologram 150 above the surface of the device 100. The image or video on the display 160 may be related to the hologram 150 or appear to interact with the hologram 150. For example, the display 160 may show ground and buildings moving as a hologram 150 of a dragon flies over the ground and buildings. As another example, the display 160 may show statistics of a sports game or video game that change as a hologram 150 of one or more players play a game.

Glasses

In one example, a user may wear glasses with special lenses (such as 3D stereoscopic glasses, polarized lenses, left eye lens may be different than the right eye lens) to help them see the hologram 150 above the device 100.

Physical Object

In one example, a user may put a physical object (such as a white cube, sphere or other shape) on the top surface 160 of the device 100, and the components 110 may project images and video onto the shape.

Sensors

Everything described above with device 10 in FIGS. 1A-1B may be implemented with and/or adapted for device 100 in FIG. 1C. For example, similar to the description above with device 10 in FIG. 1A, the device 100 in FIG. 1C may have one or more sensors 140 that detect conditions and/or objects around the device 100. Depending on the detected conditions or objects, the device 100 may cause the light generating components 110 to change one or more parameters, such as intensity or color. For example, the sensors 140 may detect a finger or other object moving toward the hologram 150, and a character or object in the hologram 150 may move or react visually and/or emit a sound.

Multiple Devices

As another example, similar to the description above with 2 devices 10, 20 in FIG. 1B, two or more devices 100 may be placed near each other, such that 2 holograms of 2 devices appear to interact with each other.

Power

As another example, the device 100 may receive power from one or more sources, such as a power outlet, solar power or other light sources, another device, or a power docking station or pad. When the device 100 runs low on power, the device 10 may cause the projected image or video 150 to change or display a low power message or symbol.

2. Glasses that Generate Visible Information on Lenses

FIG. 2A shows a back view and FIG. 2B shows a top view of a pair of glasses 200 with one or more projectors 202 that project information and/or images onto the lenses 208 (or on a screen or display on the top, bottom, or side of the lenses) for a user to see and still allow a user to see the user's environment through the lenses 208. The projectors 202 may include one or more of the projectors 16 or light-generating components 110 described above. Although the word "glasses" is used, the lenses 208 do not have to correct a user's vision, such as nearsightedness or far sightedness.

The projected information or images may relate to an object or place that the user sees through the lenses 208. The projected information or images may be off to the side or on the top or bottom so as not to obscure the view of the user.

Sensors

The glasses 200 may have one or more sensors 210, such as a camera, to capture an image or video or what the user sees through the lenses 208. Besides a camera, the sensor 210 may include one or more other sensors that sense a condition (e.g., lighting, temperature, humidity) or an object (such as a restaurant, a hotel, a street name, a tourist attraction, a gas or particles in the air, such as plant pollen, dust, pet dander, etc.), which may cause the glasses 200 to react or display information.

Transceiver

In one configuration, the glasses 200 includes a wireless transceiver 206 (e.g., cellular, WiFi) to transmit and retrieve information to and from a cell phone, a base station, a server, a network, and/or the Internet. In another configuration, the glasses 200 communicate via Bluetooth or NFC with a wireless transceiver 908 in a mobile device 900 (FIG. 9) to transmit and receive information through a network to a server. The transceiver 200 may transmit a request for information about an object or place sensed by the sensor 210 (that the user sees through the glasses 200), and receive information about that object or place.

Other Features

The glasses 200 may have fiber optic components to carry electrical signals through the frame of the glasses.

The glasses 200 may have background or ambient light blockers and/or noise cancellation to improve a user's viewing and/or audible experience.

The glasses 200 may be controlled by buttons on the glasses 200 and/or a mobile device with a touchscreen, keypad or mouse.

The glasses 200 may include (or attach to) one or more ear pieces or a headset 204 to provide audible sounds to the user. The audible information may include music or a narration of what the user is seeing through the glasses.

The glasses 200 may provide warnings about places or objects around the user seen by the sensor 210.

The glasses 200 may provide information (such as clues to a question, player statistics, keys to unlock a treasure chest) related to a game that the user is playing. The game can be a physical game or a virtual game.

FIG. 2C shows glasses 225 may have 2 sets of lenses (and/or 2 sets of frames with lenses): a first set of lenses 220 to correct for a user's nearsighted or far sightedness vision, and a second set or lenses 222 to display information. The second set 222 may slide up (e.g., when a button is pressed) or be pushed up (or removed completely) when not in use and pushed down when in use.

The glasses 200 may be implemented as part of a hat, headband, or helmet for sports.

Input Commands to the Glasses

A user may input commands to the glasses 200 through one or more ways. The glasses 200 may have buttons or a touch pad for the user to press or touch. The glasses 200 may have a microphone and voice recognition to receive spoken user commands. A device 900 (FIGS. 9 and 10) in wired or wireless communication (e.g., WiFi or Bluetooth) with the glasses 200 may have buttons or a touchscreen to receive user commands.

Behavior Recognition and Recommendation

Sometimes it is desirable to help or interact with other people, especially when a person is in an unfamiliar city, region, or country. The glasses 200 may allow a user to quickly recognize another person's behavior, such as a health problem, and recommend a way for the user to help or interact with them.

Figure 10:
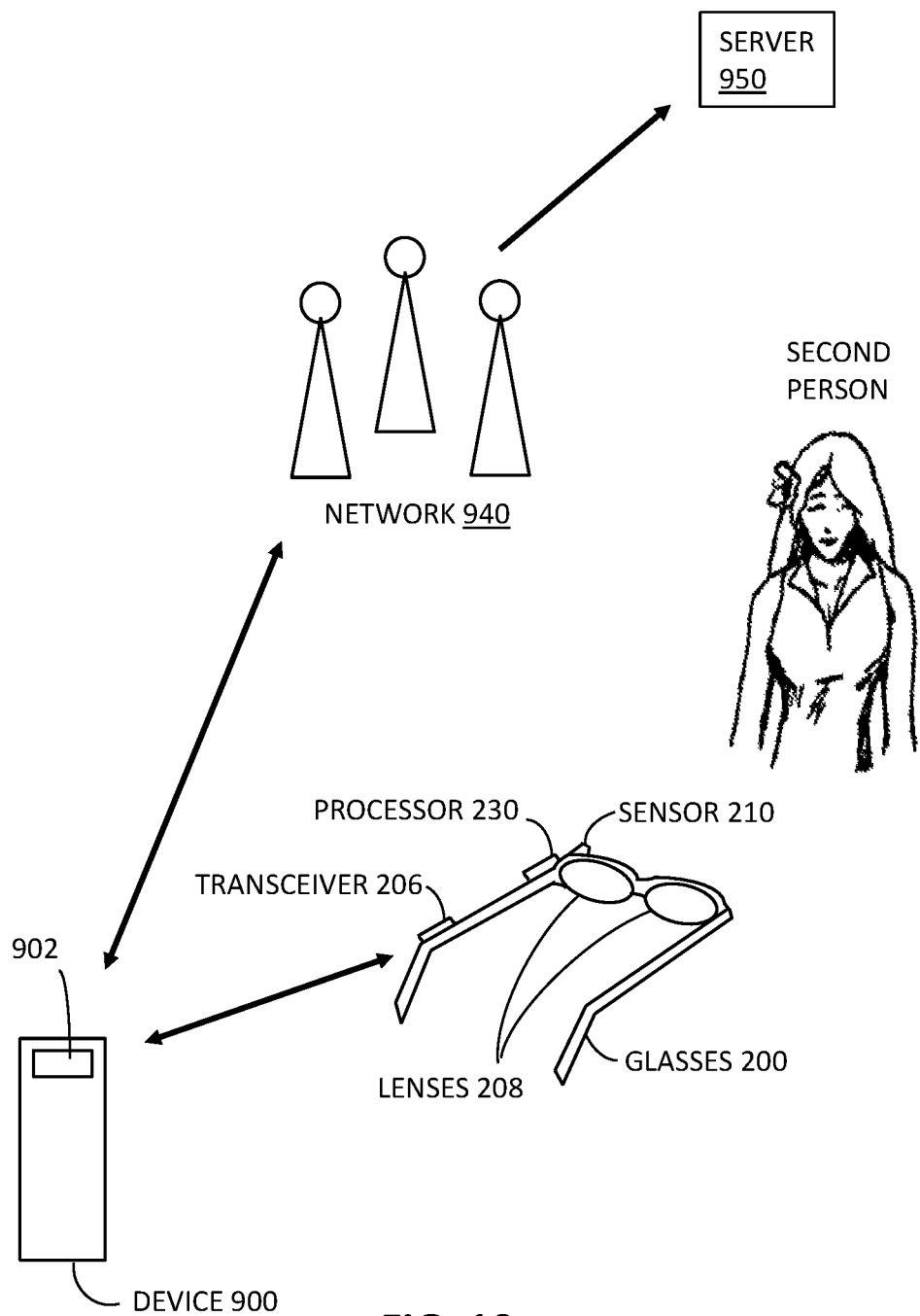
FIG. 10 shows a pair of glasses of FIG. 2A, a device, a network, and a server.

FIG. 10 shows a pair of glasses 200, a device 900 in communication with the glasses 200, a network 940 in communication with the device 900, and a server 950 in communication with the network 940. In FIG. 10, a user wears the glasses 200 and looks at a second person in front of the user. The sensor 210 of the glasses 200 captures one or more images of the second person's body posture, position, movement, action, gesture, facial expression, or body language (individually or collectively called "behavior") (block 1200 in FIG. 12).

Figure 12:
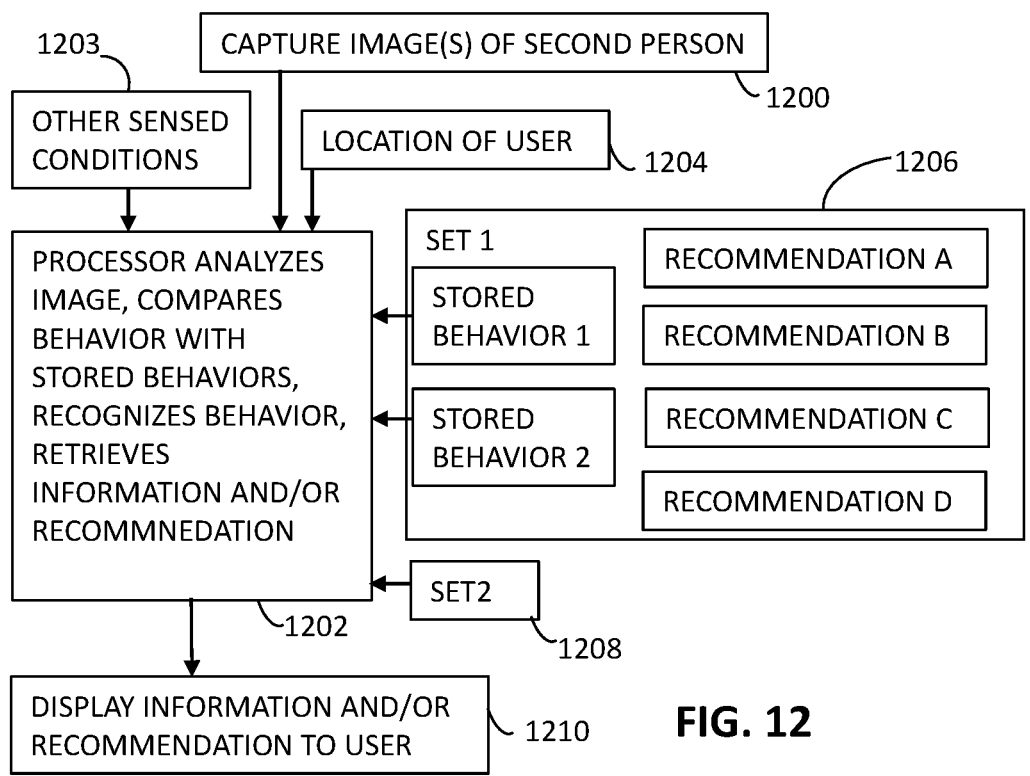
FIG. 12 shows functions that may be performed by the glasses of FIGS. 2A and 10.

A processor receives the one or more images from the sensor 210 and analyzes, recognizes, and/or interprets the behavior of the second person (block 1202 in FIG. 12). The processor may include one or more of the following (alone or in combination): a processor 230 on the glasses 200 coupled to the sensor 210, a processor 902 in the device 900 in communication with the glasses 200, or the server 950 in communication with the glasses 200 via the device 900 and the communication network 940, such as a cellular network.

Figure 11:
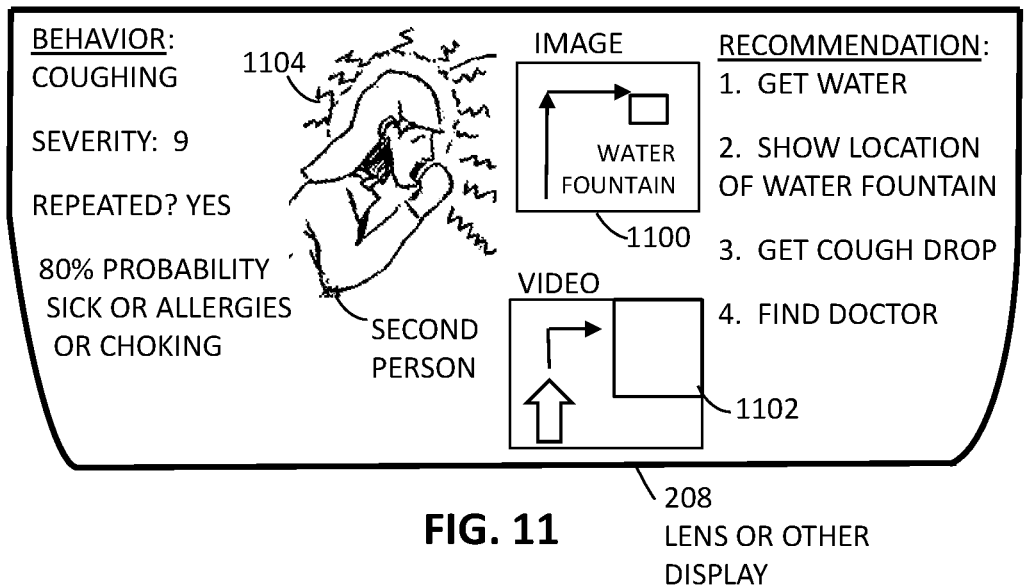
FIG. 11 shows information displayed on one or both lenses of a pair of glasses.

The processor 230 causes the glasses 200 to display information (such as a word, halo, glowing outline, icon, flashing light, or symbol) on or near the person on one or both lenses 208 of the glasses 200, or a small screen in front of the glasses 200, as shown in FIG. 11 (block 1210 in FIG. 12). In addition to or instead of displaying information, the glasses 200 may emit one or more sounds, such as a word, musical tone, or other sound, depending on the recognized behavior. The glasses 200 may display a recommendation for the user to help or interact with the second person, as shown in FIG. 11 and described in more detail below.

The glasses 200 may allow a user to activate and de-activate this behavior recognition and recommendation feature.

Recognizing a Sick Person

For example, if a person is sneezing, sniffling, or coughing, the glasses 200 can display a word "sick" above the person, a colored halo 1104 (in FIG. 11)(halo can be constant or flashing) around the person's face or head, or a sick person icon or symbol above the person, as shown in FIG. 11. The glasses 200 may display a _% probability or degree of sickness based on how many symptoms are recognized and/or how severe the coughing and sneezing are, as shown in FIG. 11.

If the second person sneezes or coughs into their hand and then touches an object, such as a door handle, a table, or a bowl, then the glasses 200 can display a warning word above the object, a red halo (constant or flashing) around the object, an icon, or a symbol. This allows the user to avoid touching the object (and potentially getting exposed to germs) touched by the second person.

Other Recognized Behaviors

Other examples of recognized behaviors and words that potentially describe the behaviors include: eyes staring off in a direction away from the glasses 200 (bored or disinterested), eyes opened wide (surprised, excited or interested), eyes squinting at a faraway object (nearsightedness) or an object nearby (farsightedness), eyes looking at the ground and hands checking pockets, bag or purse (lost something), hand supporting chin or side of a face (bored or tired), hand rubbing head (worried, concerned, or headache), hand rubbing eyes (tired, lack of sleep), slouching shoulders (bored, disinterested, fatigue), eyes wide open, hands grabbing throat (choking), exhaling loudly (disappointed, anxious), rapid hand motions (excited or agitated), hands in pockets (relaxed or trying to look relaxed), arms crossed (defensive), hands on hips (angry, confrontational, in command), tapping foot or fingers (anxious or nervous), repeatedly checking watch in a short period of time (anxious, waiting for something), arm stretched upward (trying to reach something), hand behind back (potentially carrying a weapon), eyes closed (resting, tired, or asleep), walking stiffly (uncomfortable shoes, injured leg), hand rubbing back or leg plus agonized facial expression (leg or back pain).

The glasses 200 may update displayed information about the second person after observing two or more behaviors. For example, if the second person coughs once, the display may show "sick or allergies or choking," as shown in FIG. 11. But if the second person clears her throat (and maybe drinks water) and does not cough again, the glasses 200 may update the display to show "not sick" or "just cleared her throat."

The glasses 200 may recognize a second person who is drunk (under the influence of alcohol or other drug) or a car driven by a drunk driver, such as a car that is swerving back and forth.

Behavior Analysis

As described herein with reference to FIG. 10, the word "processor" may refer to one or more of the following: the processor 230 on the glasses 200, the processor 902 in device 900, and/or the server 950.

The processor may analyze a facial expression and coloration (red cheeks, normal complexion, or pale) of the second user. The processor may analyze light reflections and shadows on or around the second person and their clothing. The processor may analyze an amount of perspiration of the second person.

The processor may compare the second person's behavior to a set of behaviors stored in a memory, such as a database or library, to find the best matching behavior (blocks 1202 and 1206 in FIG. 12). If there are two or more behaviors stored in the memory match or resemble the second person's detected behavior, the processor may cause the glasses 200 to display words for both behaviors. For example, in FIG. 11, the glasses 200 displays "Sick or allergies or choking" next to the second person coughing. Alternatively, the processor may use other factors, such as a past behavior and/or regional customs, to select one of the stored behaviors for the glasses 200 to display to the user.

The processor may compensate for a person's characteristics, such as age, height, size, weight, clothing, etc. when searching through the set of stored behaviors. For example, a shorter person's behavior may be less noticeable or more noticeable compared to a tall person, depending on the behavior.

People may have different behaviors and customs in different cultures, ethnicities, countries or regions. The processor may have a universal set of stored behaviors for all countries or regions, or a specific set of behaviors and customs for a specific culture, ethnicity, city, region, or country, as shown by set 1 1206 and set 2 1208 in FIG. 12.

In one configuration, some common behaviors may be stored in the processor 230, more behaviors may be stored in the processor 902, and even more behaviors may be stored in the server 950.

Two or More Cameras

In one configuration, the glasses 200 may have two or more cameras to capture images of a second person from two different views, which may provide more information about the second person's behavior than a single camera.

Camera Behind the User

In one configuration, the glasses 200 may have one or more cameras on the side of the glasses 200 or on the back of the user's head to capture images to the sides and/or behind the user.

Sensing Other Conditions Besides Behavior

In addition to (or instead of) recognizing behavior, the glasses 200 may have sensors to sense other conditions (block 1203 in FIG. 12), such as a microphone to hear the second person coughing, speaking, shouting, etc. The sensor 210 may have one or more sensors to sense a temperature of the second person, for example, to detect if the second person has a fever. The sensor 210 may sense a heart rate or an amount of perspiration on the head, neck, and arm pits of the second person. The sensor 210 may sense the speed of a person moving his head, hand, arm, leg, foot, etc.

Predicting the Second Person's Next Behavior

In one configuration, the glasses 200, processor 902 or server 950 may predict the second person's most likely next behavior. For example, a person who sneezed may look for a Kleenex. A person who spilled a drink may look for a napkin. A person coughing may look for something to drink or a cough drop. A person who lost something may start looking for it on the ground. A person pushed or bumped by another person may utter an angry word or seek to retaliate. The glasses 200 can display a word or symbol showing the second person's most likely next behavior and recommend an action to a user.

Recommending how to Help or Interact with the Second Person

As shown in FIGS. 11 and 12, after recognizing a behavior of the second person, the glasses 200 may recommend to the user how to help or interact with the second person, e.g., what to do and when to do it, by displaying a word, a phrase, a symbol, an image 1100, or a video 1102 (which can repeat 2 or 3 times) to the user. In addition to or instead of displaying a recommendation, the glasses 200 may emit audible words to the user, such as "ask her if she needs water."

For example, if the second person coughs or clears his/her throat as shown in FIG. 11, the glasses 200 may display one or more recommendations to the user to offer a glass of water, show the second person where the nearest water fountain is located, get a cough drop, or find a doctor. If the second person sneezes, the glasses 200 may recommend getting a Kleenex or napkin.

If the second person lost an object (contact lens, ear ring, ring, coin, etc.), the glasses 200 may calculate how the object dropped from a certain height, how the object likely bounced on the ground, and hit another object such as the second person's leg, a chair, or a bag. The glasses 200 may display to the user likely locations where the lost item may be found.

Other examples of recommendations may include: ask if the second person is hurt, help the second person carry a heavy object, make a friendly greeting, make eye contact, smile, shake hands, do a first bump, raise your hand with palm open facing up or to the side, pat the second person on the back, nod your head, salute, bow your head, bow upper torso, continue to bow (e.g., don't make direct eye contact) until the second person leaves or performs a certain action, etc., step back (to give the second person some space), sit down (to appear less threatening), put your hands on the table (to appear less threatening or more relaxed), open hands and arms (to welcome or invite the second person).

The recommendation may also show the user what NOT to do. For example, in some cultures, people are not supposed to touch other people at any time, or during a period of time, or in a particular place.

The recommendation may be based on local, cultural, ethnic, or regional customs, depending on the location of the user and/or the appearance of the second person. The glasses 200 or device 900 may have a GPS chip (or recognize the user's surroundings) to determine the user's location (block 1204 in FIG. 12). Thus, the server 950 and/or device 900 may store two or more recommendations for each stored behavior, as shown in FIG. 11 and block 1206 of FIG. 12. For example, for a second person who appears to be angry (hands on hips, raised voice, angry facial expression), the recommendation could be a pat on the back, a bow, a smile, or ask a question, depending on the user's location and/or ethnicity or nationality of the second person.

Warning the User

The glasses 200 may display a warning sign and/or emit a warning sound if the second person exhibits behaviors of being sick or poses a threat to the user, such as reaching for a weapon. The warning sign or sound may become more intense if the second person approaches the user or exhibits more behaviors.

Different Modes to Display Different Types of Information

A user may not wish to see all information generated by the glasses 200 related to every recognized behavior, which could be overwhelming. The glasses 200 may allow the user to select one or more modes for displaying different types of information. For example, a user can select a "help" mode for the glasses 200 to display only recommendations on how to help other people. A "warning" mode may display only behavior information of people that may threaten the health or safety of the user. A "sales" mode may display only recommendations to speak with certain people who appear interested in the user, a product, or a service. A "fully active" mode may display all behavior information.

Analyze Crowd Quickly to Identify a Person to Help

The glasses 200 (alone or in combination with the device 900 and/or server 950) may analyze two or more people (such as a crowd of people) faster than a normal person can, and identify a person to help. The glasses 200 may scan a crowd and quickly determine who is angry, sad, tired, bored, disinterested, interested in meeting the first person, potentially dangerous, sick, etc.

Recognize Behavior of Animals

In one configuration, the glasses 200 may recognize the behavior of animals, such as a dog, a cat, a bird, or a lizard. For example, the glasses 200 may recognize that a dog is wagging its tail while barking, which indicates the dog may be friendly or wants to play. This would allow a user to interact more with their own pets and pets of other people.

Instruct a User how to Operate a Car, Machine, or Play a Game

In one configuration, the glasses 200 may identify objects around the user and recognize that the user is in a car, on a motorcycle, or standing near a machine. The glasses 200 may display information on how to operate the car or machine by highlighting buttons to press, levers to pull or push, control switches to flip, etc. The glasses 200 may display a sequence of actions.

The glasses 200 may identify objects around the user and recognize that the user is trying to play a sport, a video game, or a board game (such as chess or Monopoly), or the user may ask the glasses 200 for help. The glasses 200 may display words or symbols and/or emit sounds to instruct the user how to play the game.

Detect User Behavior

In one configuration, the glasses 200 may detect user behavior (such as titled head resting on the user's hand or coughing) and suggest an action (such as get some rest or get some water at a fountain down a hall and around a corner).

Rewind & Analyze

Sometimes, a person is in a crowded place with a lot of activity and does not notice another person's behavior, such as a person who is lost, injured, or stealing a wallet or purse.

In one configuration, the glasses 200 constantly records and erases a loop of video for a period of time, such as 5 minutes, 30 minutes, an hour, or 24 hours. When the user says a trigger word or phrase (set by the manufacturer or set by the user; it should be a word or phrase that is not commonly said) and "rewind," the glasses 200 rewinds the video, until the user says "pause," "stop," "play," or "play slowly." This allows a user to go back and see behavior and events that the user may have missed the first time when the user looked at a scene.

The glasses 200 may allow a user to select a part of the image to zoom-in and analyze a specific person or object, and then zoom back out. For example, the user can zoom-in a particular quadrant (e.g., user says "zoom-in" and "top left," "top right," "bottom right," "bottom left") or on a particular object or person by using voice commands, touching a button or touchpad on the glasses 200, or touching the device 900.

3. Sensors for Sports

College and professional sports (such as basketball and football) sometimes have controversial foul calls (ticky tack fouls or phantom fouls) or no-calls when there actually was a foul. For example, during a Sacramento Kings vs. Los Angeles Lakers playoff game in the late 1990s, the referees called Mike Bibby for a foul when Kobe Bryant was the one who elbowed Bibby in the face, and Bibby was clearly bleeding. As another example, Vlady Divac fell down and drew a foul on an opposing player when in fact that player did not even touch Divac.

Even instant replay may not be able to determine exactly what happened. For example, a ball goes out of bounds with 30 seconds left in a NCAA Final Four game, and the officials cannot determine who touched the ball last. One camera shows one player touched the ball last, but another camera shows another player from the other team touched the ball last. As another example, a running back charges into a group of offensive linemen, blockers, defensive linemen, and linebackers on a 1-yard line, and it is impossible to see whether the ball crosses the goal line, even with multiple cameras at different angles. If the ball did not cross the goal line, then where should the player be marked as down?

Figure 3A:
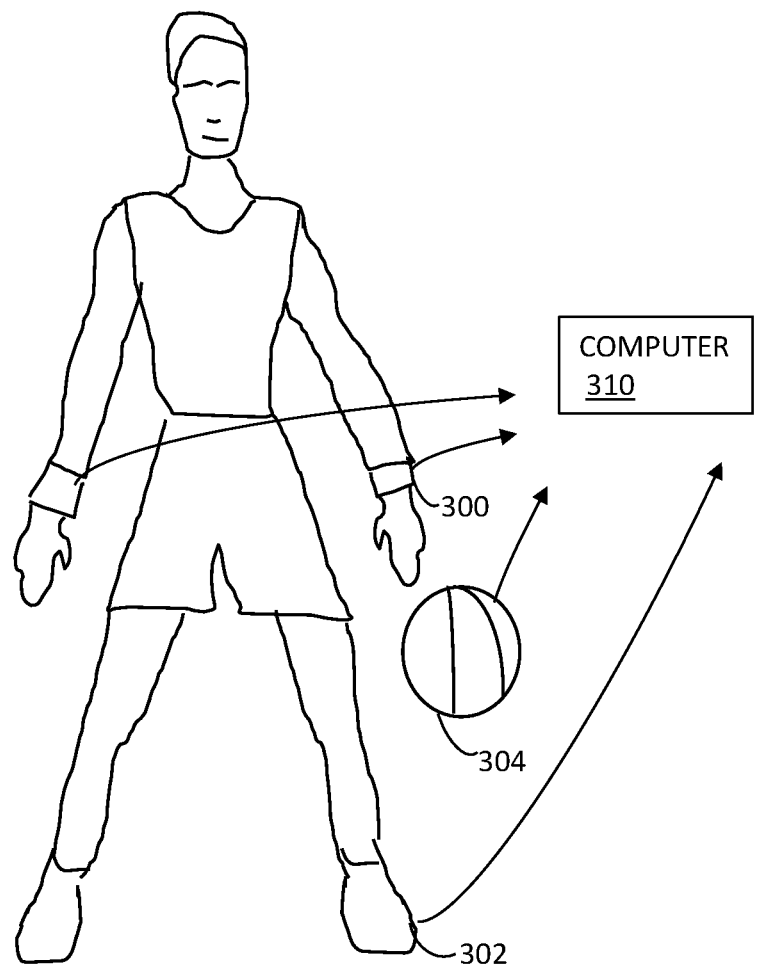
FIG. 3A shows sensors embedded in a player's clothes or gear.

Sensors on sports players, objects such as balls, or the court or field can improve a game by making more accurate calls (or helping officials make more accurate calls) and reduce human error. FIG. 3A shows sensors 300, 302 that may be very small and embedded in a player's uniform, jersey, pants, protective pads, socks, sneakers, wristbands, gloves, headbands, protective eyewear, facemasks, helmets, etc. In addition to or instead of wearing sensors during a game, a player can wear a suit that tracks and records or captures the player's movements (motion capture).

Figure 3B:
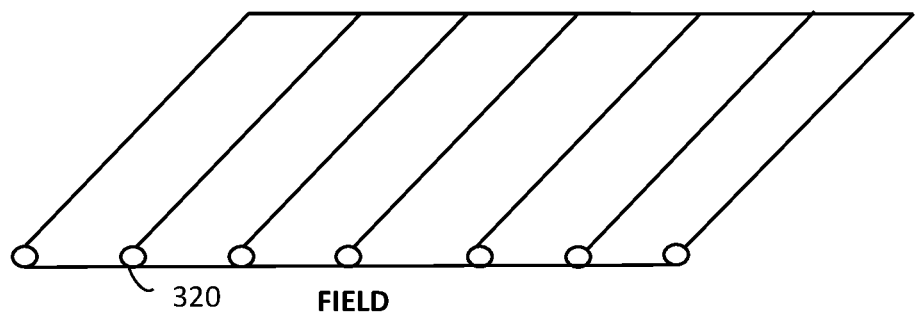
FIG. 3B shows sensors placed on lines or markers of a field or court.

Sensors 304 may also be placed in a ball. FIG. 3B shows sensors 320 that may be placed on lines (side lines, goal lines, back of end zones, 3-point lines) or markers of a field, court, out of bounds, basketball rim, backboard, and other places.

The sensors 300, 302, 304, 320 may sense or measure one or more conditions, such as pressure (force), frictional force, heat, location, position, vibration, motion, light (visible and/or non-visible, such as infrared) and/or a magnetic field generated by a magnet on a player or ball or field of play. Two or more sensors may be able to detect a signal strength or position of each other.

The sensors 300, 302, 304, 320 may comprise any component or material (or a combination thereof) that can sense or measure the conditions above. Some examples may include transducers, transceivers, magnetic strips, RFID or NFC tags, miniature cameras, microchips, resistors, inductors, power sources (batteries), circuits, flexible circuits, processors, memory, wires, etc. The sensors 300, 302, 304, 320 may have a casing made out of a durable material, such as plastic, metal, or fiberglass. The sensors 300, 302, 304, 320 may be elastic or bendable.

The sensors 300, 302, 304, 320 may be tamper resistant. For example, if there is any tampering, the sensors may transmit a sign to the computer 310 or have a seal that breaks or have a color that changes. The sensors 300, 302, 304, 320 may be waterproof.

The sensors 300, 302, 304, 320 may transmit data to computer 310 and/or store it in a recordable medium to be read by another device, such as computer 310. The sensors 300, 302, 304, 320 may encode or encrypt data first before transmitting it to the computer 310 for security and accuracy.

A computer (or group of computers) 310 collects data from the sensors 300, 302, 304, 320 on players and/or objects, such as the court, field, and ball. The computer 310 may analyze the data and perform calculations to determine precise locations and positions of players and objects in a game.

After analyzing the data, the computer 310 may display or audibly announce a result, such as a foul (or no foul) on a player, a player stepping out of bounds with or without a ball, a ball out of bounds last touched by a specific player, a player who jumped offsides, a touchdown, a fumble, a ball at a specific number yard line, a passing interference, holding, chop block, etc.

In one example, the sensors and computer 310 are used simultaneously with a team of human officials. In another example, the sensors and computer 310 are only used when the officials and instant replays are not conclusive.

The computer 310 may automatically track which players are in a game for each team based on identification codes on their sensors, or a user may input the names or numbers of the players when they enter and leave a game.

Before a game, the computer 310 may gather information about a player's height, weight, strength, vertical jump, long jump, etc. to better simulate or analyze data collected in the game.

One potential advantage is the sensors and computer 310 may be more accurate (no biases or emotions), faster, and less expensive than human officials and instant replay.

4. Sensors in Car to Detect Drunk Driving

Drunk driving is dangerous to drivers, passengers, and everyone on the street. There is not enough police to see and stop all drunk drivers. After a drunk driving accident, people wish there were more ways to prevent drunk driving.

Figure 4:
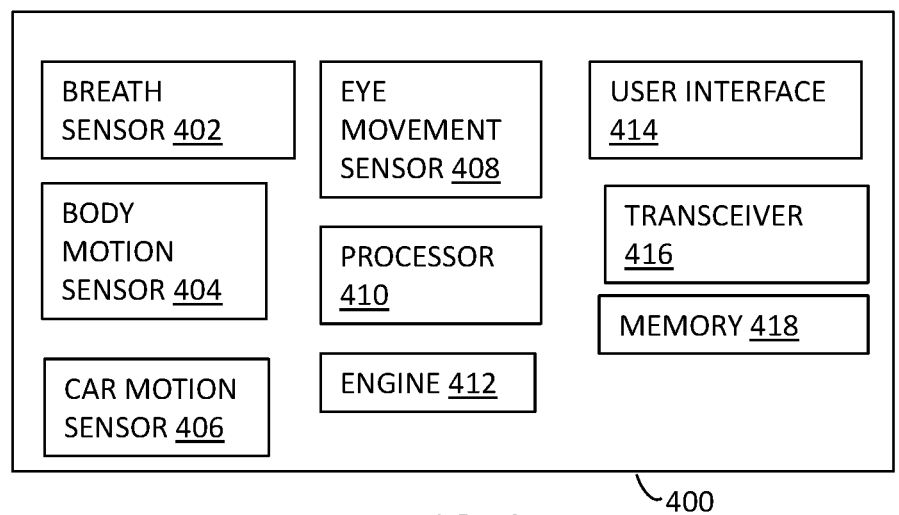
FIG. 4 shows a car with a system that has one or more sensors.

FIG. 4 shows a car with a system 400 that has one or more sensors 402-408 to detect drunk driving. The sensors 402-408 may include: a breath sensor 402 to detect (or estimate) blood alcohol level; a body motion sensor 404 to detect movements or postures (e.g. slumping) of the driver; a car motion sensor 406 to detect driving behavior that may indicate drunk driving (such as drifting into another lane and sudden swerves); and an eye movement sensor 408 to detect eye movements and/or reaction speed that may indicate drunk driving. One purpose for having multiple sensors 402-408 is to prevent a drunk driver from disabling, bypassing or avoiding one of the sensors 402-408. For example, if the driver disables or bypasses breath sensor 402, the other sensors 404-408 may still detect that the driver is drunk.

These sensors 402-408 may send data to a processor 410, which analyzes the data. Depending on the data and settings (set by the manufacturer, dealership, user, state), the processor 410 may initiate one or more actions, such as: display a warning message to the driver and/or passengers on a user interface 414; turn off the car engine 412; and/or instruct the transceiver 416 to call a friend, family member, or other person to help the driver get home.

The warning message (visual and/or audible) may advise the driver to call another driver, drink some water and eat food to sober up, advise the driver of police checkpoints, etc.

In one example, if the sensors 402-408 detect that the driver is clearly drunk and unable to drive safely (e.g., blood alcohol level over a maximum threshold), the processor 410 may call the police if the driver still tries to drive the car after displaying or emitting warning messages.

The user interface 414 may include one or more of the following: a dashboard warning light, a liquid crystal display (LCD), a light emitting diode (LED), a touchscreen, and/or a speaker to deliver an audible warning message or sound.

Some or all of the components in FIG. 4 may be portable and transferred from one car to another car. The components may be used or installed in a car of a person on probation or arrested for driving under the influence (DUI). The system 400 may send an alert to the police via the transceiver 416 if a user tries to tamper or disable with the system 400.

This system 400 can save the lives of drivers, passengers, and everyone on the street who could be hurt by drink drivers. This system 400 can also prevent property damage.

Location-Specific Communication Device

Announce Our Presence to People at a Location

Sometimes two people (family, friends, work colleagues or acquaintances) are at the same restaurant, store, amusement park, or comic book convention, such as Comic-con, but they do not know it until days, weeks or months later. Sometimes, it would be nice to know who is at a specific location, so we can say hello to family and friends and enjoy activities together.

Figure 5:
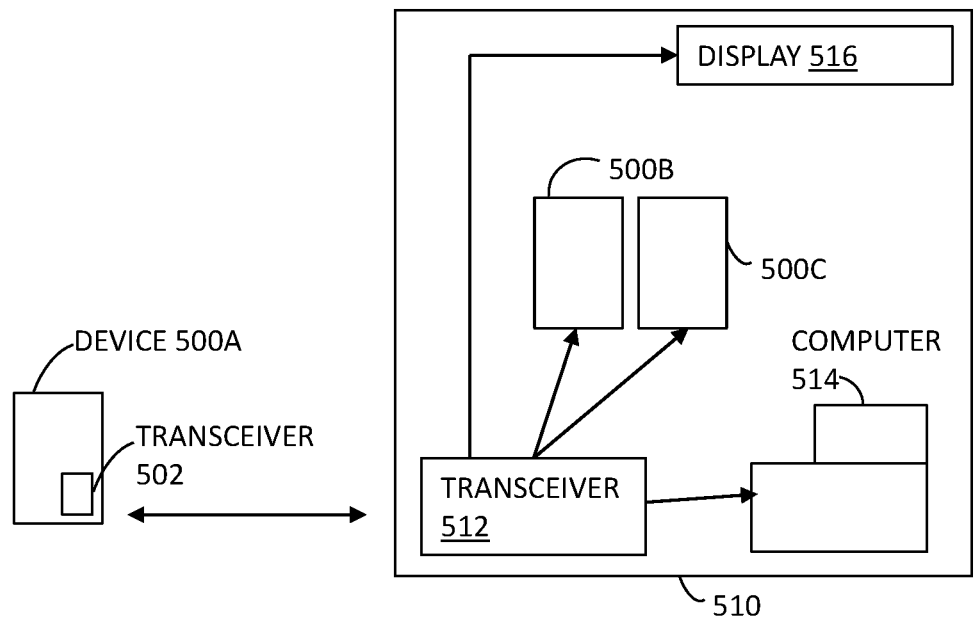
FIG. 5 shows a device with a transceiver communicating with another device.

FIG. 5 shows a device 500A (such as a mobile phone, tablet, laptop, microchip, wristwatch, credit card, key chain, or wallet) with a transceiver 502 that sends a signal to announce a user's presence at a location 510, such as a restaurant, store, mall, gym, or amusement park. The announcement can be made to a wide audience (advertising to all potential clients) or a small audience (contacts stored in the person's device 500A, Facebook friends, or other family and friends selected by the user).

In one configuration, the device 500A has a transceiver 502 that transmits a signal wirelessly (cellular, WiFi, Bluetooth, RFID/NFC, infrared) with an identification of the user (such as a name, phone number, and/or email address) to a location-specific transceiver 512. The transceiver 512 transmits the identification to one or more other devices, such as other mobile devices 500B, 500C, a banner, TV, a display or screen 516, or a desktop computer or kiosk 514.

The device 500A may have one or more default settings and information (e.g., no announcement unless activated), and a user may change some or all of the settings and information. For example, the user can activate or de-activate the announcement feature, designate which friends and family will receive the announcement, what the announcement will say, what information to broadcast widely (e.g., business card information, such as name of business, type of business, title, licenses, phone number, email address, web site, resume, LinkedIn profile), and what information to send only to selected people (e.g., phone number, email, photo). When the user enters a new location (such as a mall or restaurant), the device 500A may ask the user whether the user desires to change the announcement settings or information.

The computer 514 may display a list of people and their business card information at that location. The computer 514 may group the people according to profession, such as students, lawyers, doctors, real estate professionals, retail sales, etc.

Let Friends and Family Know when we Move from Location to Location

Sometimes we would like to inform a friend, family member (such as a spouse, child, teenager, or elderly person) or co-worker of our location or movement from one location to another location, such as on a freeway, in a city, convention floor, mall, office, restaurant, house, park, or store. We may post our location on Twitter or check-in on Facebook, but this may be time-consuming since it requires a few steps. Sometimes, the locations are not accurate.

In FIG. 5, the device 500A may have a GPS chip (or read RFID or NFC tags at each location) that determines the location of the device 500A. The device 500A may transmit a signal (hereinafter "location signal") directly or through a network to other mobile devices 500B, 500C. The other mobile devices 500B, 500C may display a map and a symbol showing the location of the device 500A on the map.

The devices 500A-500C may allow users to change one or more settings. For example, the location signal from device 500A to the other devices 500B, 500C may be set to be continuous, at timed intervals, or on demand by the other mobile devices 500B, 500C. The device 500A can allow a user to activate or deactivate the location signal. But if the user of the device 500A is a child or teenager, a parent may configure the device 500A such that the location signal cannot be deactivated. The device 500A may allow a user to select 1) which people can see the location of the user and 2) at which times of the day or week. A user can set dark areas where this feature will not inform other people of the user's presence.

Tell Us where to Find an Item in a Store

Sometimes it is hard to find a product in a mall or a large store, such as Walmart, Home Depot, Fry's Electronics, etc. Sometimes the sales people are busy with other customers, busy with other tasks, on a break, or not willing to help. Time is very valuable to many consumers.

a. In one example, the device 500A in FIG. 5 has an RFID reader or scanner that can read RFID tags on products (or their packages) in a store 510, so the user can quickly find a product.

b. In another example, the device 500A has a GPS chip or other component that tracks the location of the device 500A. The device 500A wirelessly (e.g., via cellular or Wi-Fi) sends a request to find one or more products to a computer 514 in the store 510. Alternatively, when the user enters the store 510, the computer 514 may send a signal to the device 500A causing the device 500A to say or display a message, "What can I help you find?" The user can activate or de-activate the function of receiving messages from the store computer 514.

c. After receiving the user's request, the computer 514 checks a store inventory stored in a memory and sends expected locations of the products (which may or may not have RFID tags) to the device 500A. The device 500A may display a map of the store 510 and the locations (e.g., aisle and section) of the products. The device 500A may also display the shortest path and/or the path that is least congested with other consumers. Now the user of the device 500A can go directly to specific locations of the store 510 to retrieve the products. This saves time for consumers, and may allow the store to reduce its sales personnel.

The computer 514 may also tell the device 500A how the products have been rated by other consumers, make recommendations on products, whether there are coupons for certain products, which products are for sale now or will be on sale later in the week, next week or next month, location of related products (such as a person buying pants may get a location of where belts are sold).

Multi-Media Interactive Dating Experience

People watch shows like the "Bachelor" or "Real World" for the intrigue, unexpected romance, and the hope for a story-book ending.

It would be interesting if some members of the audience could join the show each week, date the people on the show, and share the intrigue, excitement, and romance in the show. It would be than just a show or a game, it would be a unique experience.

Figure 6:
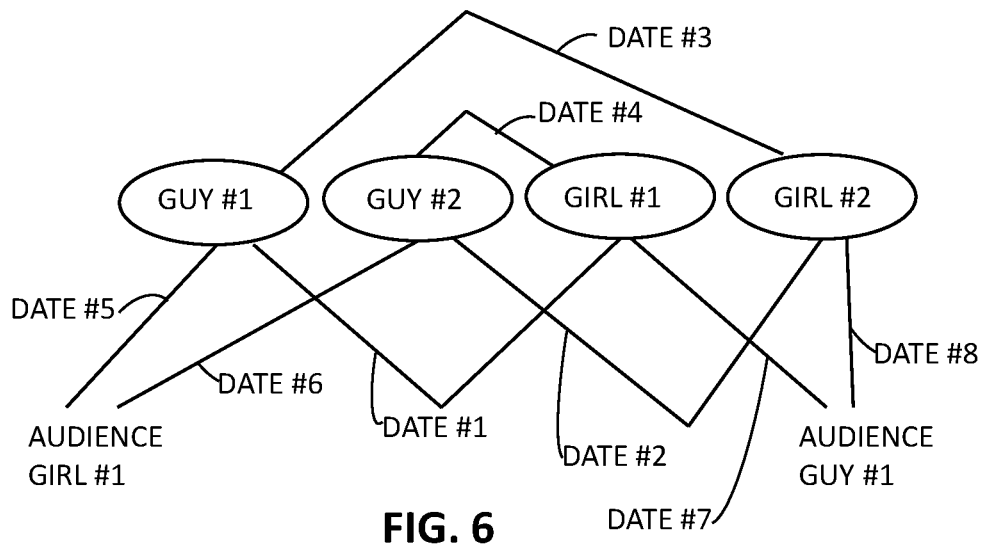
FIG. 6 shows an example of a show that starts with two guys and two girls.

FIG. 6 illustrates an example of a show that starts with two guys and two girls, who may be selected by the producers of the show based on looks, personality, occupation, interests, background, location, etc. One or more of the people may be a celebrity, such as a movie star, rock band, model, or athlete.

During the first two episodes, the two guys and two girls date each other in four dates. During the first two episodes, two new members (a guy and girl) could be selected from the audience in one or more ways: 1) at random with a lottery or sweepstakes, 2) by people on the show when audience members submit their profiles (name, photograph or video, interests, job), 3) by audience voting on a web site and/or mobile app, or 4) by the show's producers who look for certain characteristics from an interview or survey. The audience members may be selected through a screening and interview process.

The audience can watch the show on TV, online, or on their phone. There can be a weekly audience poll to decide where the dates take place—at restaurants, sporting events, parks, etc. Each member of the show can be interviewed before and after dates.

The audience can send questions to people on the show and further interact by accessing a web page or mobile app, sending emails and texts, video calls, chats. The producers may do some pre-screening of the questions and audience members.

A love triangle may develop between a guy and two girls, or a girl and two guys, which would generate more interest in the show to see who is picked.

If a guy and girl like each other, then they can leave the show, maybe with a 1-week trip to a resort in Hawaii or Caribbean. It will be interesting to see how people decide whether to stay on the show or take the trip with someone they like.

Parts of the show, such as certain dates and follow-up dates, that are especially heart-warming or funny can be put together to form a movie shown on TV or in the theater.

Mobile Phone Jamming Device
Background

Mobile phones have changed our lives by keeping us in touch with other people. But some cell phone users abuse their privileges when they are loud, obnoxious or annoying with their conversations. Some cell phone users leave their cell phones ON to receive calls in public places where other people are trying to sleep, relax or enjoy an activity, such as a quiet beach, movie theaters, musicals, operas, sporting events, like golf courses or tennis matches, church services, libraries, airplanes, trains, restaurants, etc. Probably the most annoying cell phone users are those that receive a call and carry on a conversation in public places where other people are trying to relax or enjoy an activity.

Figure 7:
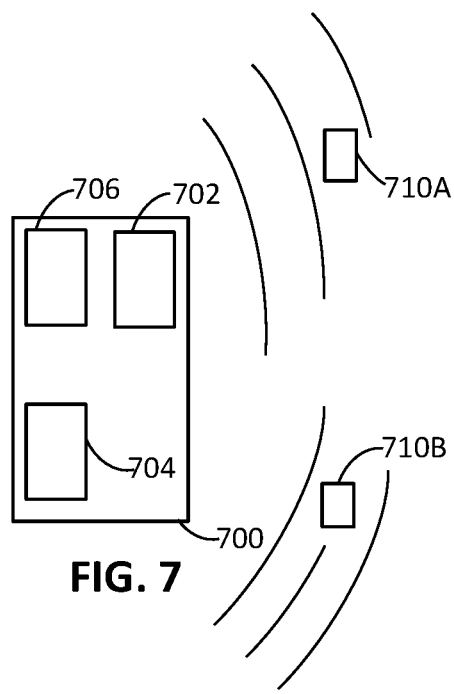
FIG. 7 shows a device that prevents people from using their cell phones.

Description—Structure a. FIG. 7 shows a device 700 that prevents people from using their cell phones 710A, 710B within a short range of the device 700. The device 700 comprises at least a transmitter 702 and an ON/OFF switch 704, such as a physical key or button, or a virtual menu item on a touchscreen. In addition to or instead of a touch-activated switch, the activation component may be voice-activated.

b. The transmitter 702 emits a signal with an equal and opposite amplitude or frequency to temporarily block or interfere with any mobile phones 710A, 710B within a configurable radius, such as 5-10 feet. The radius may be pre-determined and/or may be configurable by the user after the device 700 leaves the manufacturer. The transmitter may generate a signal that simply overpowers other radio frequency signals of cell phones 710A, 710B.

c. In one configuration, the device 700 has a receiver 706 that detects the amplitude and frequency of mobile phones 710A, 710B with the pre-determined radius. The transmitter 704 then emits a signal with an equal and opposite amplitude or frequency to block or interfere with mobile phones 710A, 710B within the pre-determined radius.

Description—Function a. The user may verbally warn cell phone users within the radius that they are too loud, and the user will activate the device 700 soon. The device 700 may send a warning signal to the active cell phones 710A, 710B within the pre-determined radius that the device 700 will be blocking signals after a time period expires, such as 10 or 30 seconds.

b. In one configuration, cell phones 710A, 710B with their signals blocked by the device 700 will not drop their calls if the cell phones 710A, 710B move out of range of the device 700 within a time period such as 5-20 seconds.

Motion Detection and Alert System
Background a. A user may leave a car at the mall or a shopping plaza or over the weekend at an airport, a train station, a bus station, a recreational facility, an amusement park, the mall, etc. When the user discovers the vehicle is missing, the user has no idea when the car is stolen. The user reports the car is stolen to police, but the user cannot tell the police what time the car was stolen. It could have been 10 minutes ago or 10 hours ago.

b. The problem with anti-theft systems like LoJack is the user has no idea when the car is stolen. The user must report the car is stolen before the anti-theft device may be used by the police. During that time, the thief may have torn the car apart, sold the car, or deactivated the Lojack tracking system.

Summary a. FIG. 8A shows a device 800 that can sense when a user's item (such as a car) is moved without the user's presence. The device 800 calls or sends a text message to the user's mobile phone 806, land-based phone, base station 804 or a police station. A car may have more than one such device 800.

b. FIG. 8A shows a car, but the device 800 may be used with any user item or object that may be set in a location and stolen, such as a truck, motorcycle, bicycle, boat, cell phone, tablet, lap top, PDA, wrist watch, jewelry (e.g., in gym lockers), purse, book bag, golf clubs, skis, tennis racket, sunglasses, coat, etc. The device 800 may be attached (permanently or temporarily) to the user's item or built into the user's item by the manufacturer.

Description

Transceiver a. FIG. 8B shows the device 800 with a wireless transceiver 830 that detects when a user key 802 (which may have a RFID tag or a transmitter) is within range, such as within 2-5 meters of the device 800. The transceiver 830 may be designed or configured by the user or manufacturer to detect the user key 802 within any desired range. The transceiver 830 may receive signals from the key 802, a mobile phone 806 or a land-based phone.

b. The transceiver 830 can call, send a text message, or other notification to a mobile phone 806, a tablet computer, a land-based phone, a pager, a lap top or a PDA. The transceiver 830 may use cellular, Wi-Fi, Bluetooth or other types of communication. The transceiver 830 may have a range that is sufficient to place a call to a base station or short-range radio frequency, such as walkie talkies.

Sensor a. FIG. 8B shows the device 800 with a sensor 820 that detects a condition, such as a location or motion of an object. For example, the sensor 820 may sense motion with a gyroscope or other component(s) commonly used in smartphones and tablet computers that sense motion. In addition or instead of those components, the sensor 820 may sense motion by transmitting a constant or periodic signal or beam of radiation to a surface, such as a car tire 822 and/or the ground 824, and detecting the reflected or scattered radiation. This may be short-range such that sunlight does not overly affect the component's detection of reflected radiation. The sensor 820 may sense motion by transmitting a signal or radiation between a first part and a second part, such as a device placed between a door and a doorframe in house security alarm systems. In addition to or instead of sensing a location or motion, the sensor 820 may sense vibration and/or heat.

b. The sensor 820 may be shielded or closed when the device 800 is not activated to prevent dirt or other substances from affecting the motion detecting.

c. The sensor 820 may include a global positioning satellite (GPS) chip.

Operation a. A user parks a car, turns off the engine and moves with the key 802 and/or mobile device 806 out of range of the device 800 on the car, such as more than 2 meters. The device 800 may activate automatically or manually when the user says a voice command or presses a button on the key 802 or mobile device 806. The device 800 begins to monitor a location or position of the vehicle and detects when the vehicle starts to move. If the user brings the key within range of the device 800, the device 800 may automatically deactivate, disarm, go into a sleep or hibernation mode, or reset. Alternatively, the user may deactivate the device 800 by pressing a button on the key 802 or mobile device 806.

b. If the device 800 senses that the car moves without the key 802 or mobile device 806 within the preset range, the device 800 may call a pre-determined phone number, such as the user's mobile phone number, or send a text message. If device 800 reaches the mobile phone's voicemail, e.g., the mobile phone is busy, not activated, or the user does not answer, the device 102 may call another pre-determined number, such as a family member or "911" or a local police station.

c. The device 800 may require a user password or code (or other form of authentication to verify the user, such as a retina scan or fingerprint scan) to disarm. For example, if someone's purse is stolen, the thief cannot disarm the device 800 simply by having a person's key 802 and mobile device 806.

d. The device 800 may have a user interface that allows a user to activate or disarm the device 800, enter a user password or code, and/or select options, modes or settings from a menu.

e. As another example, the user leaves an object (such as a mobile phone, tablet, laptop, PDA, watch, purse, book bag, golf club, skis, tennis racket, sunglasses, coat or other personal item) and activates the device 800 inside or attached to the object. The device 800 may be very small and fit in any location of an object. With the device 800, the user knows exactly what time the object is moved, unlike systems like LoJack.

f. The device 800 may use one or more power sources, such as a battery or solar or light power.

The invention claimed is:

1. An apparatus comprising:
 a frame configured to be worn on a user's head;
 a camera on the frame configured to capture a video of a second person;
 a display on the frame configured to play the video for the user to see;
 a processor on the frame configured to receive a user command to pause the video being played on the display, rewind the video, and at least one of (1) play the video slowly on the display, and (2) zoom in on the second person and play the video on the display;
 a transceiver on the frame configured to transmit the video to a second device and receive, from the second device, information about a behavior of the second person determined from the video,
 wherein the display is configured to display the received information.

2. The apparatus of claim 1, wherein the processor is configured to allow the user to select a part of the video that the user zoomed in on the second person for the transceiver to transmit to the second device to determine the behavior of the second person.

3. The apparatus of claim 1, wherein the received information comprises at least one of a word, an image, a second video, a halo around the second person, a glowing outline, an icon, a flashing light, and a symbol.

4. The apparatus of claim 1, wherein the received information comprises a recommendation to the user to interact with the second person based on the determined behavior of the second person.

5. The apparatus of claim 1, further comprising a memory configured to record and erase a loop of the captured video.

6. The apparatus of claim 1, wherein the transceiver is configured to receive, from the second device, information about two behaviors of the second person determined from the video, the display being configured to display the information about the two behaviors to the user.

7. The apparatus of claim 1,
 wherein the transceiver on the frame is configured to receive from the second device (1) a health condition of the second person based on the behavior of the second person determined from the transmitted video, and (2) a plurality of recommendations to the user to help the second person in response to the health condition; and
 wherein the display on the frame is configured to display the health condition and the plurality of recommendations to the user, each recommendation comprises at least one of a word, a phrase, a symbol, a second image, or a video.

8. The apparatus of claim 7, wherein the processor is further configured to scan a crowd of people and identify a person in the crowd for the user to help.

9. The apparatus of claim 7, further comprising a sensor configured to sense a condition, the condition comprising at least one of temperature, humidity, particles in the air, sounds of the second person, a temperature of the second person, perspiration of the second person, and speed of movement of the second person.

10. The apparatus of claim 7, wherein the processor is further configured to determine a location of the apparatus, wherein the transceiver is configured to transmit the location of the apparatus to the second device, and receive recommendations for the user based on the second person's behavior and the location of the apparatus.

11. The apparatus of claim 7, further comprising a speaker configured to play audio recommendations to the user to help the second person in response to the health condition.

12. The apparatus of claim 1, further comprising a speaker configured to emit sounds related to the information received by the transceiver.

13. The apparatus of claim 1, wherein the processor is configured to determine a location of the apparatus, wherein the transceiver is configured to transmit the location of the apparatus to the second device, and receive information about the second person's behavior determined from the video and the location of the apparatus.

14. The apparatus of claim 1, wherein the transceiver is configured to receive information related to a game that the user is playing, wherein the display is configured to display the received information related to the game.

15. The apparatus of claim 1, further comprising a sensor configured to sense a condition, the condition comprising at least one of lighting, temperature, humidity, particles in the air, sounds of the second person, a temperature of the second person, a heart rate of the second person, perspiration of the second person, and speed of movement of the second person.

16. The apparatus of claim 1, wherein the transceiver is configured to receive information about an object near the second person in the video, wherein the display is configured to display the received information about the object.

17. The apparatus of claim 1, wherein the processor is configured to receive an input from the user to select at least one mode from at least two modes for displaying different types of information.

18. The system of claim 17, wherein the second device is configured to (1) analyze an object near the second person in the video and (2) transmit information about the object to the transceiver, wherein the transceiver is configured to receive information about the object from the second device, wherein the display is configured to display the received information about the object.

19. A method comprising:

capturing a video of a second person with a camera on a frame worn on a user's head;

playing the video on a display on the frame for the user to see;

receiving a user command at a processor on the frame to pause the video being played on the display, rewind the video, and at least one of (1) play the video slowly on the display, and (2) zoom in on the second person and play the video on the display;

transmitting the video from a transceiver on the frame to a second device;

receiving, from the second device, information about a behavior of the second person determined from the video; and displaying the received information on the display.

20. A system comprising:

a first device; and a second device in communication with the first device;

wherein the first device comprises:

a frame configured to be worn on a user's head;

a camera on the frame configured to capture a video of a second person;

a display on the frame configured to play the video for the user to see;

a processor on the frame configured to receive a user command to pause the video being played on the display, rewind the video, and at least one of (1) play the video slowly on the display, and (2) zoom in on the second person and play the video on the display;

a transceiver on the frame configured to transmit the video to the second device and receive, from the second device, information about a behavior of the second person determined from the video, wherein the display is configured to display the received information.

\* \* \* \* \*